US008494250B2

(12) United States Patent
McDermott et al.

(10) Patent No.: US 8,494,250 B2
(45) Date of Patent: Jul. 23, 2013

(54) ANIMATION FOR CONVEYING SPATIAL RELATIONSHIPS IN THREE-DIMENSIONAL MEDICAL IMAGING

(75) Inventors: Bruce A. McDermott, Bellevue, WA (US); Mervin Mencias Smith-Casem, Renton, WA (US); Patric Ljung, Princeton, NJ (US); Stefan Wiesner, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1232 days.

(21) Appl. No.: 12/351,638

(22) Filed: Jan. 9, 2009

(65) Prior Publication Data

US 2009/0304250 A1 Dec. 10, 2009

Related U.S. Application Data

(60) Provisional application No. 61/059,648, filed on Jun. 6, 2008.

(51) Int. Cl.
*G06K 9/00* (2006.01)
*G06K 9/32* (2006.01)
*G06T 15/00* (2006.01)
*G06T 17/00* (2006.01)
*G06T 15/10* (2006.01)

(52) U.S. Cl.
USPC ........... 382/154; 382/293; 382/295; 382/296; 345/419; 345/420; 345/427

(58) Field of Classification Search
USPC .................. 382/154, 293–297; 345/419, 420, 345/427
See application file for complete search history.

(56) References Cited

U.S. PATENT DOCUMENTS

| 6,334,847 | B1 | 1/2002 | Fenster et al. |
|---|---|---|---|
| 7,033,320 | B2 | 4/2006 | Von Behren et al. |
| 7,782,319 | B2 * | 8/2010 | Ghosh et al. .................. 345/427 |
| 2005/0228280 | A1 | 10/2005 | Ustuner et al. |
| 2005/0283075 | A1 | 12/2005 | Ma et al. |
| 2007/0046661 | A1 | 3/2007 | Ma et al. |
| 2007/0083099 | A1 | 4/2007 | Henderson et al. |
| 2008/0009722 | A1 | 1/2008 | Simopoulos et al. |
| 2009/0195536 | A1 * | 8/2009 | Louise et al. .................. 345/419 |

OTHER PUBLICATIONS

Hemminger et al., "Assessment of real-time 3D visualization for cardiothoracic diagnostic evaluation and surgery planning", Journal of Digital Imaging, vol. 18, No. 2, pp. 145-153, Jun. 2005.*
Yoshida et al., "Three-dimensional computer-aided diagnosis in CT colonography", Multidimensional Image Processing, Analysis, and Display: RSNA Categorical Course in Diagnostic Radiology Physics 2005, pp. 237-251, 2005.*
Chen et al., "Spatial transfer functions—a unified approach to specifying deformation in volume modeling and animation", Volume Graphics, 2003.*

* cited by examiner

Primary Examiner — Anand Bhatnagar
Assistant Examiner — Soo Park (57) ABSTRACT

Spatial relationships are conveyed in three-dimensional ultrasound imaging. To transition a volume rendering from one view to another view, the transition is animated, showing rotation. For example, the user examines one diagnostic view, but decides to examine another diagnostic view. Upon selection of the other diagnostic view, the volume rendered image appears to rotate. The rotation from one view to another shows the spatial relationship between the views. The user may then examine the static volume rendering at the desired view with an appreciation of the relationship with the previously examined static view.

14 Claims, 6 Drawing Sheets

ANIMATION FOR CONVEYING SPATIAL RELATIONSHIPS IN THREE-DIMENSIONAL MEDICAL IMAGING

RELATED APPLICATIONS

The present patent document claims the benefit of the filing date under 35 U.S.C. §119(e) of Provisional U.S. patent application Ser. No. 61/059,648, filed Jun. 6, 2008, which is hereby incorporated by reference.

BACKGROUND

The present embodiments relate to medical diagnostic imaging. In particular, different three-dimensional views (two-dimensional images of different views of a three-dimensional object are shown).

Ultrasound or other medical imaging modalities may be used to scan a patient. For example, echocardiography is a commonly used imaging modality to visualize the structure of the heart with a multi-planar reconstruction (MPR). Because the echo is often a 2D projection of the 3D human heart, standard views are captured to better visualize the cardiac structures. For example, in the apical four-chamber (A4C) view, all four cavities, namely left and right ventricles, and left and right atria, are present. In the apical two-chamber (A2C) view, only the left ventricle and the left atrium are present. Another example is imaging the intracranial structures of a fetus. Three standard planes are acquired with different orientations for visualization of the cerebellum, the cisterna magna, and lateral ventricles.

Ultrasound data may be acquired at a sufficient rate to allow three-dimensional ultrasound imaging in real-time. For example, a combination of one or more MPR's, which show images of specific planes through a 3-dimensional volume and a volume rendering (VR), which shows a 3-dimensional representation of a view of the data from a user-selectable viewing direction, is provided. Non-real-time three-dimensional ultrasound imaging may also be provided. In other examples, VR is provided without MPR.

Different viewing options are available for VR. For example, the VR may be rendered with a viewing direction orthogonal to any of the MPR slices, with a clip plane placed at the location of the MPR slice to remove data in front of the clip plane from the volume rendering. The user studies the VR. The user may switch the viewing direction and clip plane location to create different views that allow diagnosis. To transition between the different views, the VR jumps to a new viewing direction and clip plane location following a new user selection. This jump can be distracting or disorienting to the user. Alternately, the user may use a trackball or other user interface control to incrementally apply rotation to change the clip plane location or viewing direction. User changes that incrementally change the clip plane or viewing direction may lack repeatability, preventing the user from consistently achieving the desired views.

BRIEF SUMMARY

By way of introduction, the preferred embodiments described below include methods, computer-readable media and systems for conveying spatial relationships in three-dimensional medical imaging. To transition a VR from one view to another view, the VR is animated to smoothly rotate to the new viewing direction. For example, the user examines one diagnostic view, but decides to examine another diagnostic view. Upon selection of the other diagnostic view, the VR image appears to rotate. The gradual rotation from one view to another shows the spatial relationship between the views. The user may then examine the static VR at the desired view with an appreciation of the relationship with the previously examined static view.

In a first aspect, a method is provided for conveying spatial relationships in three-dimensional medical imaging. A first three-dimensional representation of a first diagnostic view of at least a portion of the acquired data set is displayed. The first three-dimensional representation is at a first viewing angle. An indication of a second diagnostic view of the portion is received. A transition from the first diagnostic view to the second diagnostic view is animated. The transition includes a plurality of intermediary three-dimensional representations of the portion of the acquired data set. Each of the intermediary three-dimensional representations of the portion corresponds to different intermediary viewing angles. A second three-dimensional representation of the second diagnostic view of the portion of the acquired data set is displayed after the transition. The second three-dimensional representation is at a second viewing angle different than the first viewing angle, and the different intermediary viewing angles are different than the first and second viewing angles.

In a second aspect, a system is provided for conveying spatial relationships in three-dimensional medical imaging. A memory is operable to store data representing a volume of a patient. A processor is operable to generate a plurality of three-dimensional representations of the volume from the data. Each of the three-dimensional representations has a different viewing angle relative to the volume. A timer is operable to cause static display of an initial three-dimensional representation of the plurality for a first period and a final three-dimensional representation of the plurality for a second period. The timer is operable to cause display of a sequence of three-dimensional representations of the plurality between the initial and final three-dimensional representations. Each of the three-dimensional representations of the sequence is displayed for a time less than the first and second periods. A display is operable to display the initial three-dimensional representation, the sequence of three-dimensional representations, and the final three-dimensional representation.

In a third aspect, a computer readable storage medium has stored therein data representing instructions executable by a programmed processor for conveying spatial relationships in three-dimensional medical imaging. The storage medium includes instructions for receiving user input indicating a change of a three-dimensional rendered image from a first view to a second view, and animating the change of the three-dimensional rendered image from the first view to the second view such that three-dimensional rendered image appears to gradually transition from the first view to the second view rather than jump directly from the first view to the second view.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND SPECIFIC EMBODIMENTS

With the present invention, the user of the ultrasound or other medical imaging system or an offline review workstation may better understand the spatial relationships between various views of 3D data. By using animation to slowly rotate or tilt the 3D volume rendering when transitioning from one viewing direction of a 3D volume to another view, the viewer may more easily understand the spatial relationship between the different viewing directions. The start of the animation may be triggered by a single button push or other activation, simplifying user control as compared to manual rotation and resetting of the clip plane.

Figure 1:
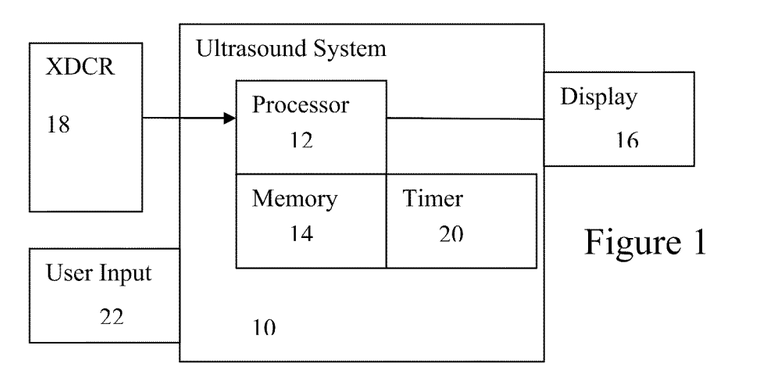
FIG. 1 is a block diagram of one embodiment of a medical imaging system.

FIG. 1 shows a medical diagnostic imaging system 10 for conveying spatial relationships in three-dimensional medical imaging. The system 10 is a medical diagnostic ultrasound imaging system, but may be a computer, workstation, database, server, or other imaging system. Other medical imaging systems may be used, such as a computed tomography or a magnetic resonance system.

The system 10 includes a processor 12, a memory 14, a display 16, a transducer 18, a timer 20, and a user input 22. Additional, different, or fewer components may be provided. For example, the system 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the system 10 does not include the transducer 18. The timer 20 is shown as separate, but may be part of the processor 12.

The transducer 18 is a piezoelectric or capacitive device operable to convert between acoustic and electrical energy. The transducer 18 is an array of elements, such as a multi-dimensional or two-dimensional array. Alternatively, the transducer 18 is a wobbler for mechanical scanning in one dimension and electrical scanning in another dimension.

The system 10 uses the transducer 18 to scan a volume. Electrical and/or mechanical steering allows transmission and reception along different scan lines in the volume. Any scan pattern may be used. In one embodiment, the transmit beam is wide enough for reception along a plurality of scan lines, such as receiving a group of up to 20 or more receive lines for each transmission. In another embodiment, a plane, collimated or diverging transmit waveform is provided for reception along a plurality, large number, or all scan lines.

Ultrasound data representing a volume is provided in response to the scanning. The ultrasound data is beamformed, detected, and/or scan converted. The ultrasound data may be in any format, such as polar or Cartesian coordinates, Cartesian coordinate with polar coordinate spacing between planes, or other format. In other embodiments, the ultrasound data is acquired by transfer, such as from a removable media or over a network. Other types of medical data representing a volume may also be acquired.

The memory 14 is a buffer, cache, RAM, removable media, hard drive, magnetic, optical, or other now known or later developed memory. The memory 14 may be a single device or group of two or more devices. The memory 14 is shown within the system 10, but may be outside or remote from other components of the system 10.

The memory 14 stores the ultrasound data. For example, the memory 14 stores flow components (e.g., velocity, energy or both) and/or B-mode ultrasound data. The medical image data is a three-dimensional data set, or a sequence of such sets. For example, a sequence of sets over a portion, one, or more heart cycles of the heart are stored. A plurality of sets may be provided, such as associated with imaging a same person, organ or region from different angles or locations. The data represents a volume of a patient, such as representing a portion or all of the heart.

For real-time imaging, the ultrasound data bypasses the memory 14, is temporarily stored in the memory 14, or is loaded from the memory 14. Real-time imaging may allow delay of a fraction of seconds, or even seconds, between acquisition of data and imaging. For example, real-time imaging is provided by generating the images substantially simultaneously with the acquisition of the data by scanning. While scanning to acquire a next or subsequent set of data, images are generated for a previous set of data. The imaging occurs during the same imaging session used to acquire the data. The amount of delay between acquisition and imaging for real-time operation may vary, such as a greater delay for initially locating planes of a multi-planar reconstruction with less delay for subsequent imaging. In alternative embodiments, the ultrasound data is stored in the memory 14 from a previous imaging session and used for imaging without concurrent acquisition.

The memory 14 is additionally or alternatively a computer readable storage medium with processing instructions. The memory 14 stores data representing instructions executable by the programmed processor 12 for conveying spatial relationships in three-dimensional medical imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical image data. The processor 12 is a single device, a plurality of devices, or a network. For more than one device, parallel or sequential division of processing may be used. Different devices making up the processor 12 may perform different functions, such as a scanning controller and an image generator operating separately. In one embodiment, the processor 12 is a control processor or other processor of a medical diagnostic imaging system, such as a medical diagnostic ultrasound imaging system processor. In another embodiment, the processor 12 is a processor of an imaging review workstation or PACS system. The processor 12 operates pursuant to stored instructions to perform various acts described herein, such as obtaining data, generating three-dimensional representations (i.e., two-dimensional image of a view rendered from volume information), animating transition between views, and/or controlling imaging.

The processor 12 generates a plurality of three-dimensional representations of the volume from the data. Any type of rendering may be used, such as surface rendering or projection rendering. For example, a viewing direction is established relative to the volume. Rays extend in parallel or diverging from a virtual viewer through the volume. Data along each ray is used to determine one or more pixel values. For example, the first datum along each ray that is above a threshold is selected and used for that ray. For viewing an internal portion of the volume, the volume may be clipped. The data in the portion of the volume behind the clip plane is used for rendering. The clip plane and the viewing direction are independent. A clip plane is used to remove a portion of the volume data from the volume rendering calculations. The viewing direction can be adjusted without changing the clip plane location. The changing of the viewing direction is animated independently of any changes in the clip plane. Other rendering and/or clipping may be used, such as using alpha blending, clip boxes, parallel clip planes, and/or fragment and vertex processing.

Each three-dimensional representation has a viewing angle relative to the volume. For the animation, initial, final, and a sequence of renderings in between each have different viewing angles. To show rotation, the viewing angle is incremented along one or more axes. Any size rotation increment and any amount of time between successive renderings may be used. For example, the displayed 3D volume is re-rendered at the display rate of the monitor, e.g. ~60 Hz. Depending on the rate of change of the viewing direction, the viewing direction of the rendered volume may be changed at a rate up to the display rate. The viewing angles may be evenly distributed for the animation, but irregular distribution may be used, such as representing more rapid rotation through greater step size at one or more points in the animation. A pause in the change of the viewing direction may also be used to emphasize a particular view. The angles may be along a shortest path directly around the volume. The initial and final viewing angles are known, such as associated with predetermined or standard viewing directions. In alternative embodiments, the rotation is indirect, such as moving the viewing angles sequentially along two or more different axes.

Each of the three-dimensional representations is rendered from the same (frozen case) or different data (live or continuous playback case). For example, the initial three-dimensional representation is rendered from data representing half of the volume (e.g., the back half of the heart where the A4C clip plane is used as the clipping plane). The final three-dimensional representation is rendered from data representing a different half of the volume (e.g., the left half of the heart where the A2C clip plane is used as the clipping plane). The transition between sub-volumes from the initial to the final rendering is gradual, such as adding some of the final sub-volume and removing some of the initial sub-volume with each intermediate rendering or change in viewing angle. In another embodiment, the entire volume is rendered from the viewing direction for the initial three-dimensional representation, providing an exterior view of the volume. The rotation then occurs. Once rotated, then the final sub-volume is used. To avoid jumps between the initial sub-volume and the full volume for rotation and between the full for rotation and the final sub-volume, a plurality of renderings may be performed with a gradual increase or decrease in the data, such as adding orthogonal layers of data for each rendering. Any combination of jumps, data or sub-volume growth or shrinking may be used to transition from the initial view to the final view.

For MPR sync animation, there are two components that change—clip plane and viewing direction. For example, the clip plane is changed immediately or initially, and the viewing direction gradually changes with a timer controlling the rate of change to the new viewing direction.

In one example embodiment, the processor 12 generates multi-planar reconstructions and a volume rendering of the volume data, such as of the heart. Three MPR (multi plane reconstruction) images are generated. A fourth window or portion of the display is used for a three-dimensional representation of the volume. The three-dimensional representation may be rendered for any desired view, such as a view corresponding to placing a clip plane at the location of one of the MPRs. The viewing direction for the volume rendering is orthogonal to or slightly offset to orthogonal (e.g., 5-10 degrees) to the clip plane placed at the location of the MPR in the volume data. The clip plane is used as a clipping plane with the representation rendered from data behind the clip plane from the users view point. In one example, the initial and final three-dimensional representations are three-dimensional renderings from viewing angles associated with different clip planes synchronized to the locations of specific multi-planar reconstruction. An icon is associated with each clip plane or standard view. The icon is a trigger to synchronize the clip plane to a particular MPR and start the animation sequence. This control input may be implemented in any other type of user interface control, such as a control panel button. In response to selection of a different icon, the processor 12 causes the three-dimensional representation to shift to a rendering associated with the selected view. The shift is performed as an animated rotation or transition from one view to the other, rotating the viewing angles for the three-dimensional representation in a plurality of steps.

In another example embodiment, the processor 12 generates the initial three-dimensional representation as a full view of a heart from the outside of the heart. One or move previous three-dimensional representations may be provided, such as showing a clipped rendering and jumping or transitioning to the full view in response to an indication to switch views. The full view is then divided into two separate renderings, such as one for the back half and one for the front half of the heart. A clip plane through the center, such as dividing the heart in the middle along the A4C view, of the volume defines two sub-volumes initially rendered from the same viewing angle as the full view. Three-dimensional representations are rendered for each half in sequence to show rotation. The viewing angles are shifted away from each other, causing the heart to appear to be opened up to view the interior of the front and back halves. Each sub-volume is rotated about 90 degrees through an animated sequence. The rotation of each half occurs at a same time as the other, or the rotations are performed sequentially. The final view is an interior view of each half of the heart.

The timer 20 is a clock, processor, counter, or other circuit for differentiating time segments. In one embodiment, the timer 20 is the processor 12. The timer 20 is programmable or may operate using fixed periods.

The timer 20 causes the processor 12 to statically display an initial three-dimensional representation. For diagnosis, the user views the statically displayed rendering. Any period of static display may be used, such as until the user indicates a transition. Similarly, the timer 20 causes the processor to statically display the final three-dimensional representation for any period. "Final" is used to reflect the view to which the rendering is transitioned. The final view may be an initial view for another animation or transition. The animation may or may not start from the initial view and may or may not end at the initial view. No, one, or more jumps noticeable to the user may be provided.

For animation, the timer 20 causes the processor 12 to generate a sequence of three-dimensional representations for display. The sequence represents rendering between the initial and final three-dimensional representations. Based on the timer 20, each of the three-dimensional representations of the sequence is displayed for a time less than the static displays of the initial and/or final views. The time between three-dimensional representations in the animation may be a fraction of a second, such as $1/10^{th}$ of a second or less. The timer 20 controls, in part, the rate of change in the viewing direction when transitioning from one viewing direction to another. The step size of the viewing angle transition may also affect the rate of transition. The timer 20 controls the speed of the rotation in viewing direction. This timing allows the animation to appear to rotate in real-time to the user. Any given rendering may not be displayed long enough for diagnosis, but does show the spatial transition between views. The speed is slow enough to allow the user to comprehend the change in viewing direction and quickly interpret the new anatomical perspective. Longer periods may be provided. For example, a total time for the animation from start view direction to end view direction is set. For clamshell animation, multiple timers control both viewing direction rate of change and duration of the pause at the initial position. The rate of change of the viewing direction is controlled by selecting one of several functions (i.e., the rate of change of the viewing direction may be constant, linear, or some non-linear function).

The display 16 is a CRT, LCD, plasma, monitor, projector, printer, or other now known or later developed display device. The display 16 displays the initial three-dimensional representation, the sequence of three-dimensional representations, and the final three-dimensional representation. Images, such as three-dimensional representations, are displayed by themselves or in groups. Multiple images, such as clip planes and a rendering, may be displayed in different portions of a screen of the display 16, such as in different windows.

The user input 22 is a button, slider, knob, keyboard, mouse, trackball, touch screen, touch pad, combinations thereof, or other now known or later developed user input devices. The user may operate the user input 22 to program the timer 20, set rendering values (e.g., define a clip plane, select a type of rendering, set an offset angle, or set the step size or speed for animation), or operate the system 10. The processor 12 transitions in an animation from the initial three-dimensional representation, through the sequence of three-dimensional representations, and to the final three-dimensional representation in response to user activation of the user input 22. For example, the user selects an icon, selects a clip plane image, and/or otherwise defines a viewing direction with the user input 22. In response, the processor 12 transitions through animation to the indicated view. A single input may be used to cause transition (e.g., selection of an icon) or a plurality of inputs may be used (e.g., translating or otherwise defining a clip plane or viewing direction).

Figure 2:
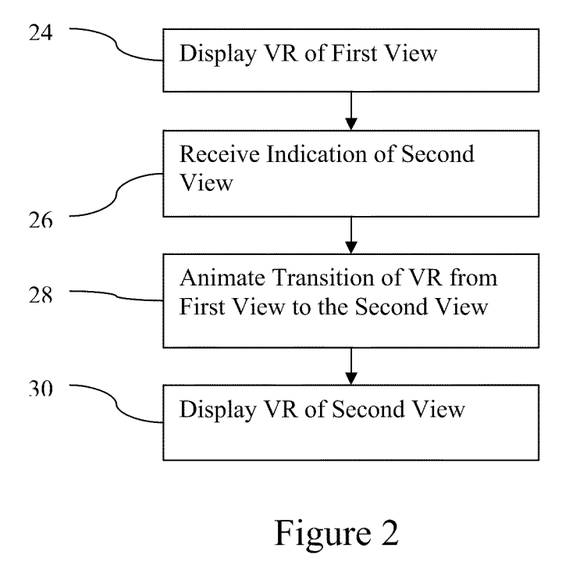
FIG. 2 is a flow chart diagram of embodiments of methods for conveying spatial relationships in three-dimensional medical imaging.

FIG. 2 shows a method for conveying spatial relationships in three-dimensional medical imaging. The method is implemented by a medical diagnostic imaging system, a review station, a workstation, a computer, a PACS station, a server, combinations thereof, or other device for image processing medical ultrasound or other types of volume data. For example, the system 10 or computer readable media 14 and processor 12 shown in FIG. 1 implements the method, but other systems may be used. The method is implemented in the order shown or a different order. Additional, different, or fewer acts may be performed. For example, act 26 is optional. As another example, scanning is performed to acquire the data used for the display in act 26.

The acts 24-30 are performed in real-time, such as during scanning. The user may view images while scanning. The images may be associated with previous performance of acts 24-30 in the same imaging session, but with different volume data. For example, acts 24-32 are performed for an initial scan. Acts 24-30 are performed for subsequent scans during the same imaging session. For real-time imaging, the volume data used for any given rendering may be replaced with more recently acquired data. For example, an initial rendering is performed with one set of data. The final rendering is performed with another set of data representing the same or similar (e.g., due to transducer or patient movement) volume. The animation may be based on one or more sets of data. In alternative embodiments, a same data set is used for all of the acts 24-30 either in real-time with scanning or in a post scan review.

For scanning, an ultrasound transducer is positioned adjacent, on, or within a patient. A volume scanning transducer is positioned, such as a mechanical wobbler or multi-dimensional array. For adjacent or on a patient, the transducer is positioned directly on the skin or acoustically coupled to the skin of the patient. For within the patient, an intraoperative, intercavity, catheter, transesophageal, or other transducer positionable within the patient is used to scan from within the patient.

The user may manually position the transducer, such as using a handheld probe or manipulating steering wires. Alternatively, a robotic or mechanical mechanism positions the transducer.

The volume region of the patient is scanned, such as scanning an entire heart or portion of the heart from the esophagus or through another acoustic window. Other organs or parts of a patient may be scanned. The wobbler or multi-dimensional array generates acoustic energy and receives responsive echoes. In alternative embodiments, a one-dimensional array is manually moved for scanning a volume.

One or more sets of data are obtained. The ultrasound data corresponds to a displayed image (e.g., detected and scan converted ultrasound data), beamformed data, detected data, and/or scan converted data. The ultrasound data represents a region of a patient. Data for multiple planar slices may be represent the volume region. Alternatively, a volume scan is used. The region includes tissue, fluid or other structures. Different structures or types of structures react to the ultrasound differently. For example, heart muscle tissue moves, but slowly as compared to fluid. The temporal reaction may result in different velocity or flow data. The shape of a structure or spatial aspect may be reflected in B-mode data. One or more objects, such as the heart, an organ, a vessel, fluid chamber, clot, lesion, muscle, and/or tissue are within the region. The data represents the region.

In act 24, an initial three-dimensional representation is displayed. Initial indicates a first representation relative to subsequent representations. The initial representation may or may not be the original representation displayed during a given imaging session or for a given volume.

The initial three-dimensional representation is of a diagnostic view. A diagnostic view is a view for study by a medical professional or other user. The diagnostic view may or may not be used for a given diagnosis. The diagnostic view is not fleeting, allowing for study, such as being a static view for two or more seconds. The diagnostic view may correspond to a plurality of renderings, such as where real-time imaging of a beating heart is provided. The view does not change, but the data used for the volume rendering changes over time. The view corresponds to a viewing angle. The viewing angle is the position of a user or screen relative to the volume to be rendered. For example, the viewing angle may be substantially orthogonal to a multiplanar reconstruction clip plane.

The data may be static as well. The representation is static by having a static viewing angle and/or static data. In other embodiments, the initial three-dimensional representation is not diagnostic, whether fleeting, randomly selected, or user selected.

In one embodiment of a diagnostic view, the three-dimensional representation is for a standard diagnostic view. The rendering or clipping plane is parallel or substantially parallel (e.g., substantially accounts for an offset to view a valve or other internal structure) to a standard two-dimensional view. For example, the clip plane corresponds to an A4C view, an A2C view, a LAX, or other standard view and the viewing direction corresponds to an orthogonal to the clip plane with or without an offset. The displayed representation may be labeled (e.g., A4C) and/or annotated (e.g., valve highlighted).

The initial three-dimensional representation is of at least a portion of the patient. The volume may represent the entire patient or part of the patient, such as an organ (e.g., the heart). The representation may be formed from an entire volume or a portion of the entire volume, such as where some portion is clipped.

In act 26, an indication of a second diagnostic view of the portion of the patient is received. The indication may be automatically generated, such as being free of user input. For example, a sequence of different views is to be provided to the user. Each view is displayed for a predetermined or programmable period. After the period, the view transitions to the another view. The processor or timer indicates that the next view is to be provided.

The indication may be from a user input. The user selects another view different than the one currently shown. For example, the user may select to synchronize the viewing direction of the volume rendering to a different multi-planar reconstruction view. The selection may be of an icon displayed adjacent a particular clip plane, a menu selection, selection of the clip plane image, or other user input. The user selects a different diagnostic view. In response, a signal is generated and received. The signal indicates selection of the view. The signal may indicate selection of a next view or selection of a particular view. A single input, such as operating a single button or clicking on an icon, may trigger transition. Multiple inputs may be used in other embodiments.

In act 28, a transition between views is animated. Rather than jumping from one view to the next, at least one intermediary three-dimensional representation is generated. The intermediary views animate the transition from one diagnostic view to another diagnostic view. The three-dimensional rendered image appears to gradually transition from the first view to the second view.

Figure 3:
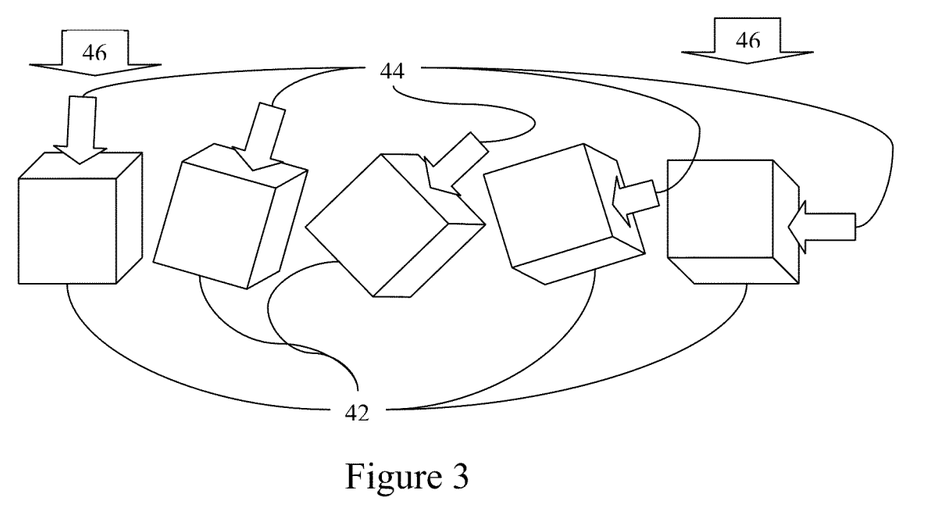
FIG. 3 is a graphical representation of rotation of a volume rendering between two views in one embodiment.

In one embodiment, the animation or gradual transition is a plurality of intermediary three-dimensional representations of the portion. Each of the intermediary three-dimensional representations and the initial and final views of the portion correspond to different viewing angles. The imaged portion, such as the heart, is rotated between the current view and the selected view. The initial, intermediary, and final three-dimensional representations are generated and displayed as a sequence. The sequence represents steps in the different viewing angles gradually changing from the initial viewing angle to the final viewing angle. FIG. 3 shows one example. The three-dimensional representation of the volume 42 is rotated. The arrow 44 represents a given viewing angle. The rotation of the volume 42 and the arrow 44 represents rotation of the three-dimensional representation. For the left most volume 42, the arrow 44 represents the viewing angle used for rendering the representation (the user's view relative to the volume is downward). The right most volume 42 shows a different face of the volume 42 directed upwards, towards the user's view position. The arrow 44 shows that the initial view angle is now perpendicular to the user's downward view angle. The three volumes 42 in between represent three or more intermediary amounts of rotation of the volume 42 relative to the user's viewpoint.

Any step size, spatial route or path, period of display of each representation, or time between representations may be used. In one embodiment, each of the intermediary three-dimensional representations is displayed for a short time such that the portion appears to rotate. For example, five or more representations are displayed every second. By having relatively small step sizes in the viewing angle, such as only a few degrees, the three-dimensional representation appears to smoothly rotate. In one alternative embodiment, the animation has varied speed of transition or size of steps between viewing angles. For example, the transition proceeds to one or more other diagnostic views, pausing on each for while (e.g., 1-10 seconds) and then proceeds to the selected view. As another example, the transition more rapidly transitions at the beginning and/or middle of the animation than at the end.

Figure 4:
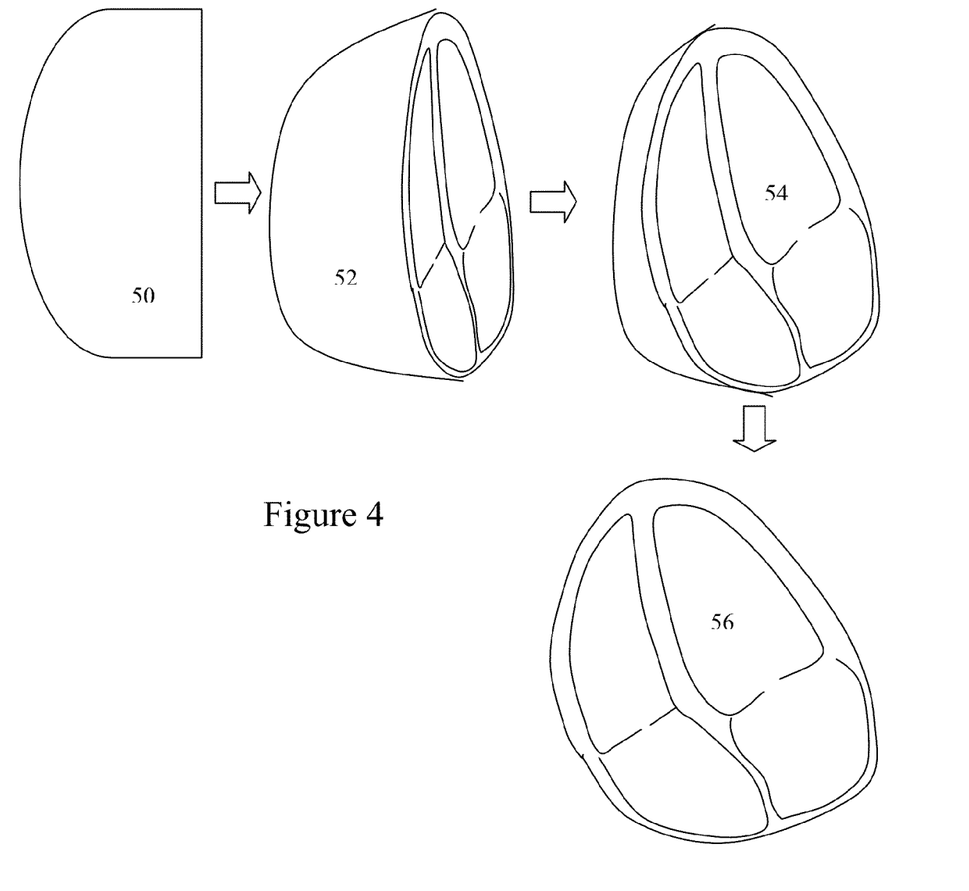
FIG. 4 is a graphical representation of rotation of a volume rendering between two views in another embodiment.
Figure 5A:
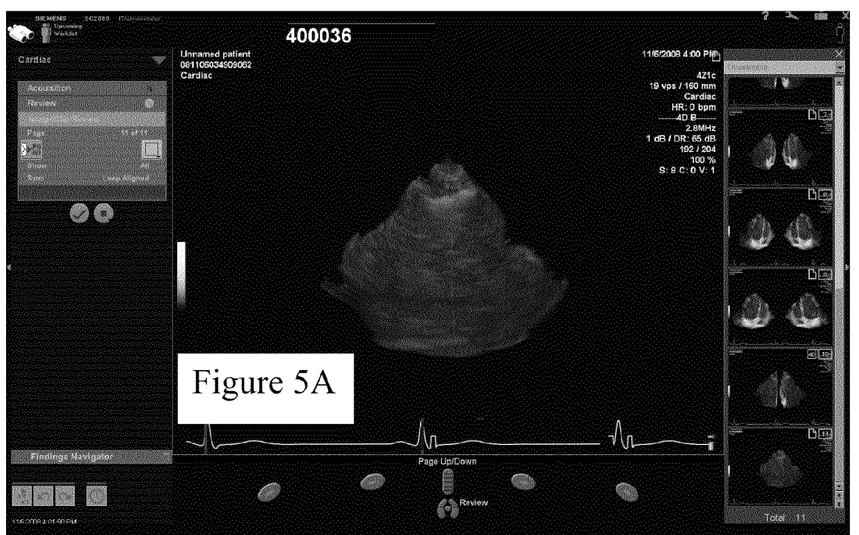
FIGS. 5A-E are medical images showing animation of opening of the heart.
Figure 5B:
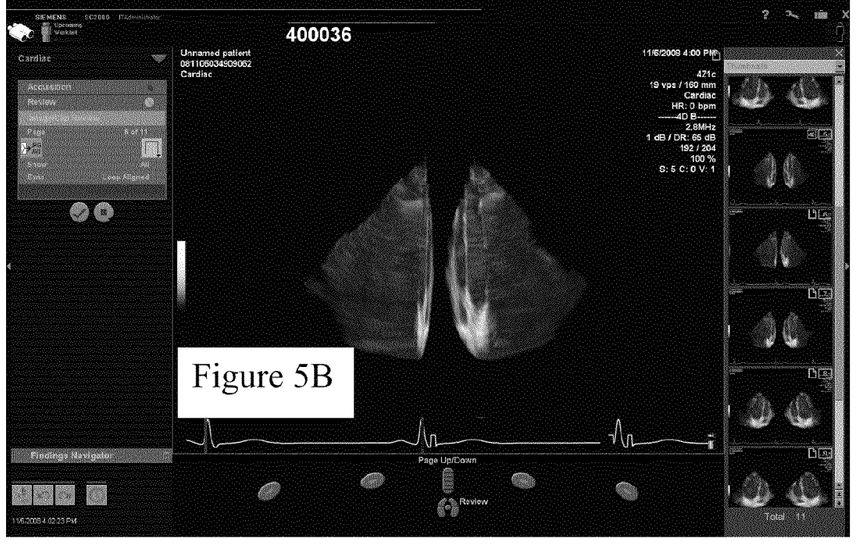
Figure 5C:
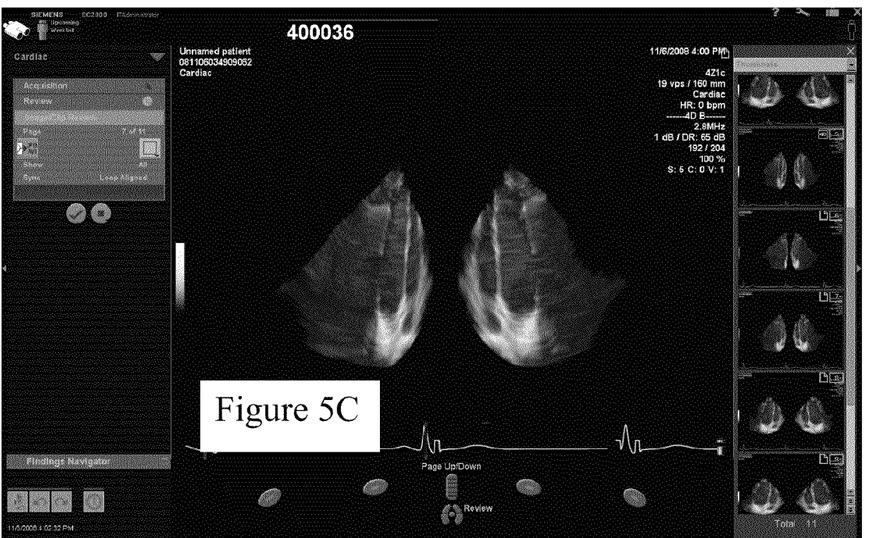
Figure 5D:
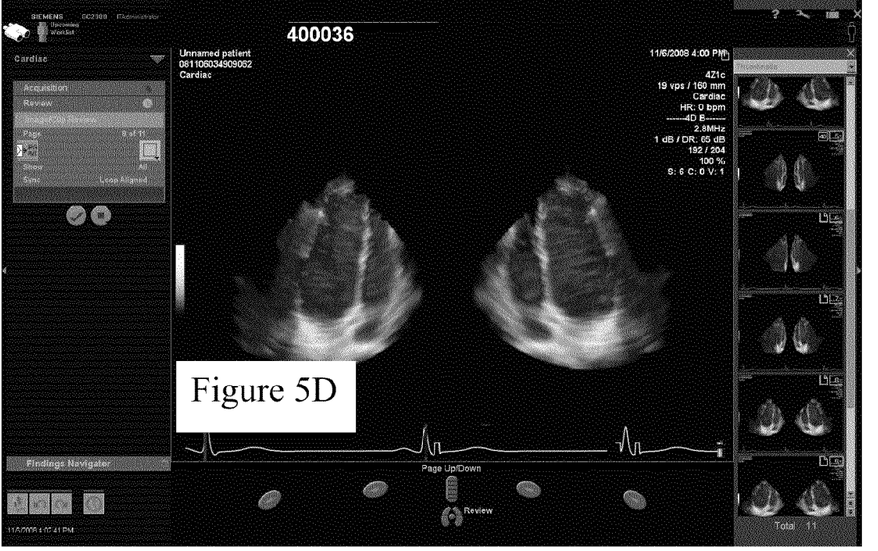
Figure 5E:
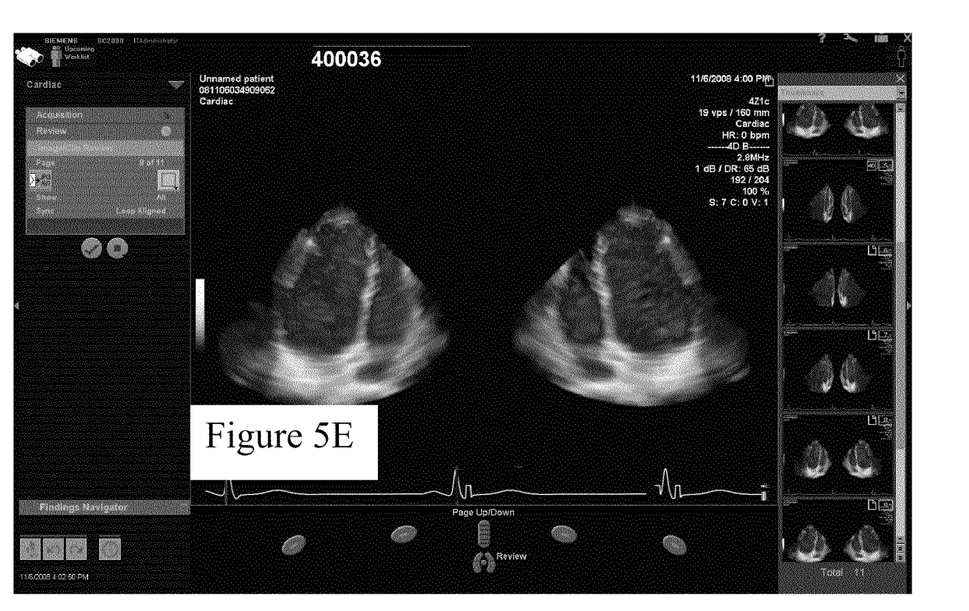

In other embodiments, a jerky or non-smooth rotation is provided. For example, a three-dimensional representation of a A2C view is displayed. The user selects an A4C view. Since these views are orthogonal to each other and rendered from different subsets of data (e.g., left half verses back half of the heart volume), the three-dimensional representation first jumps to a rendering from the full data set, showing the outside of the heart instead of the cross-section interior A2C rendering. The viewing angle is the same. Intermediary representations may be rendered from gradually increasing amount or region of the volume, such as adding data layers to transition from the cross-section data set to the full data set. The three-dimensional representation then jumps to or gradually transitions to a cross-section data set for the next view (A4C) without changing the viewing angle. FIG. 4 shows an example three-dimensional representation 50 as the A4C sub-volume of the heart before animation to the desired diagnostic view. The animation with a change in viewing angle is then performed, rotating the three-dimensional representation to the desired view. FIG. 4 shows two example three-dimensional representations 52, 54 intermediary (e.g., at 15 degrees from initial viewing angle and at 75 degrees from the initial viewing angle) to the initial representation 50 and the final representation 56 (e.g., 90 degrees from the initial viewing angle). More or fewer intermediary representations 52, 54 at different angles may be provided.

In other embodiments, the animation first rotates the angle, and then transitions to the data set or sub-volume appropriate for a given view. In yet other embodiments, the animation transitions both the viewing angle and the sub-volume at a same time or with steps interleaved with each other. In other embodiments, the whole volume or same sub-volume is used for the initial, intermediary, and final three-dimensional representations.

In act 30, the final three-dimensional representation is displayed. "Final" is used to indicate the selected view or the view to which the animation transitions. Different three-dimensional representations from different views and/or data sets may be later provided.

The final three-dimensional representation is of the same organ or portion of the body being viewed. The portion being viewed is of the same patient structure, but may rely on different data. For example, the animation transitions from a view of the back half of the heart to a left side of the heart. The clipping of the volume data set transitions as part of the animation. The final representation uses the same or different data as the initial and/or intermediary representations. For example, the clipping plane stays constant relative to the viewer during the animation, not relative to the volume data set. As the volume is rotated relative to the clip plane, data gets removed from the view as the view moves in front of the clip plane and is added to the view as the view is moved behind the clip plane.

The final three-dimensional representation is displayed after the transition, such as being a last step in the animation. The final representation is rendered with a viewing angle different than the intermediary and initial viewing angles. Each of the angles is different than all other angles of the initial, intermediary, and final renderings. In an alternative embodiment, the animation transitions through representations at a same angle, such as associated with viewing around the volume and then transitioning the final viewing angle.

The final three-dimensional representation is displayed statically. For example, the same viewing angle is used for seconds, such as at least two seconds. One or more renderings are performed during the static display. For example, a same data set is used, so only one rendering is generated and the resulting three-dimensional representation is displayed the entire time. In another example, the data changes as a function of time, such as to show the beating of the heart. The three-dimensional representation is of the same viewing angle, but the data changes to show changes in the heart from that diagnostic view over time. The three-dimensional representation is maintained at the selected view until an indication of another view is received, such as from a timer or user input. In alternative embodiments, the final three-dimensional representation is non-static, such as being within a larger animation so that the final three-dimensional representation is displayed for a similar amount of time as intermediary views within the animation.

The final three-dimensional representation is a diagnostic or other view. The diagnostic view is for study by a medical professional in order to assist in diagnosis. The diagnostic view may correspond to a standard view, such as A4C, A2C or other canonical heart view. For example, the diagnostic view is of the A4C, but with an angular offset (e.g., 5-15 degrees) from orthogonal to the A4C clip plane for better viewing of valves. Alternatively, the diagnostic view may correspond to a medical professional preferred or experimental view. Non-diagnostic final representations may be provided by random or testing selection of the viewing angle, such as associated with examining different views in machine learning in an effort to identify diagnostically significant views. The default positions of the MPRs are the standard views. The user is allowed to move the position of the MPRs relative to the volume, so that when the user synchronizes the clip plane in the volume rendering to one of the MPR planes, the user may animate to any viewing direction, not just a standard view.

One example embodiment is the use of animation for the three-dimensional representations associated with multi-planar reconstruction. A plurality of two-dimensional images representing clip planes through an ultrasound scan volume is displayed. The images are displayed at a same time, but may be displayed sequentially. For example, three two-dimensional images corresponding to substantially orthogonal clip planes at standard locations relative to the heart are displayed in three different quadrants of a screen or display arrangement. In this echocardiography example, canonical slice(s) or planes, such as apical four chamber (A4C) and apical two-chamber (A2C) views, are extracted from the data representing the volume. These anatomical planes are continuously displayed irrespective of the orientation of the transducer used in the acquisition of the volume ultrasound data. Each image is part of an overall window or background, or each image is part of an individual window or background.

The fourth quadrant or other section of the total display includes a three-dimensional representation. The three-dimensional representation is of at least a portion of the ultrasound scan volume through which the clip planes are positioned. For example, the three-dimensional representation is rendered from the data for the entire volume, showing an exterior view of the heart. The representation may be animated (e.g., slowly rotating the exterior heart view) or static. As another example, the three-dimensional representation is rendered from data for a sub-volume, such as the back half of the heart. The rendering is for a viewing angle corresponding to a predetermined or selected view, such orthogonal with or without an offset angle to the A4C clip plane (e.g., the three-dimensional representation 56 of FIG. 4).

The user selects a different view for the three-dimensional representation. For example, the user selects a displayed clip plane image, an icon for that clip plane, or a menu item from a list of views. The user may select one of three buttons to synchronize the virtual rendering or three-dimensional representation viewing direction to one of the clip planes (e.g., MPR A, B or C). The renderer supports and displays a sync icon in each MPR window. The sync icon is selected to synchronize the three-dimensional representation rendering plane and/or clip plane to the MPR clip plane whose sync icon is selected.

In response to receipt of the user input selection, the three-dimensional representation is transitioned from the current viewing angle to a viewing angle for the selected view. For example, the transition is from a rendering of one multi-planar reconstruction view (e.g., A4C) to another multi-planar reconstruction view (e.g., A2C or LAX). When synchronizing the rendering viewing direction to one of the clip planes, the system slowly rotates the XYZ coordinates of the three-dimensional representation viewing direction to the new desired direction. On selecting the MPR C button, a clip plane that corresponds to MPR C is applied to and any previous clip plane is removed from the volume data set used for the three-dimensional rendering. The three-dimensional representation is then slowly rotated to the new viewing orientation. The three-dimensional representation rotates to an orientation in which the clip plane (now synched with the selected MPR) is nearly parallel to the screen. The rotation is animated with a programmable rotation duration and acceleration and final tilt angle offset so that the VR clip plane is not completely parallel to the screen.

The animation of the three-dimensional representation is displayed along with the two-dimensional MPR images. The initial, intermediary, and final three-dimensional representations are displayed in a quadrant or other section of the display substantially simultaneously with the MPR images. The animation clarifies the spatial transition from one view to another, and the MPR images provide details about the specific views.

In another embodiment, two or more three-dimensional representations are displayed at a substantially same time. The transition is from one view to two different views. For example, the initial view is an exterior view of the whole heart from the side. As another example, the initial view is a diagnostic view with the volume clipped along a clip plane. Using either a transition or jump, the diagnostic view switches to the whole heart exterior view. Animation is used from volume rendering of the entire heart to slowly cleave the volume into two halves and open the volume similar to an opening book. In alternative embodiments, only a portion of the heart is cleaved, such as where the available data does not represent the entire heart. The data set used for rendering may be continuously updated, such as real-time scanning of the entire heart. Animating the "opening" of the dual three-dimensional representation display shows the user how the two halves of the ultrasound data fit together spatially.

The three-dimensional representation of one or both halves, once opened, represent diagnostic views. Each representation is rendered from a sub-portion of the heart. For example, the cleaving corresponds to dividing the volume in half and separately rendering a representation from the divided sub-volumes. The three-dimensional representations of the divided sub-volumes are then animated to rotate. The viewing angles are rotated in different directions relative to the volume so that the representations rotate in opposite or different directions. The viewing angles are altered separately with the same or different transition rate and/or viewing angle step size. In the heart example, the heart is divided into a front half and a back half. The representation 50 of FIG. 4 shows one such half. The two representations are then rotated from side views to a front view for the back half of the volume and a back view for the front half of the volume. FIG. 4 shows such animation for the front half. The three-dimensional representations rotate to view the insides of the heart. FIGS. 5A-E show medical image renderings of this transition.

The front and back half three-dimensional representations are displayed side by side, such as rotating from a common axis at a rear center vertical line along the volume relative to the initial whole view. The two different three-dimensional representations may be displayed in a same or different windows initially, during animation, and finally.

In one example embodiment, the three-dimensional representation is initially viewed based on a standard clip plane, such as associated with a MPR rendering. The user selects the clam shell or dual view mode. Upon enabling this viewing mode, the three-dimensional representation is animated to rotate such that the viewing direction is nearly parallel to the range-azimuth plane with the top of the volume towards the top of the screen. The view is of a left side of the heart with the top of the heart at a top of the screen and the bottom of the heart at the bottom of the screen. The three-dimensional representation may be tilted slightly with a programmable tilt angle, such as 10-15 degrees along one or two axes. In alternative embodiments, the representation jumps to this orientation. The entire (unclipped) volume is then displayed whole for a programmable duration of time. The representation jumps to or gradually transitions from a sub-volume rendering to the whole volume. The representation then divides into two representations. The separate representations are then animated to rotate to different viewing angles, appearing to open up to a programmable angular span during a programmable duration of time. The two sub-volumes pivot about a vertical axis located at the rear-center of the volume with respect to the viewer (like opening a book).

For cardiology, opposite halves of the heart are shown simultaneously. This feature could be used for other applications. For example, the gall bladder is animated to cleave and open up near gall stones. Other organs that may have a diagnostically useful interior view may likewise be animated to open. Other portions of the body may be animated to cleave and view from different directions.

Animation between views may be used in any application, such as for imaging any organ. The initial and final views may be exterior views. In one embodiment, the user manually manipulates a cut or clip plane. After viewing the two-dimensional image or three-dimensional representation based on the plane, the view is reset to a default or other view. The transition between the manual and predetermined or previous view is animated. Any transition due to selection of a different view may be animated.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for conveying spatial relationships in three-dimensional medical imaging, the method comprising:
   displaying a first three-dimensional representation of a first diagnostic view of at least a portion of the patient, the first three-dimensional representation being at a first viewing angle;
   receiving an indication of a second diagnostic view of the portion;
   animating a transition from the first diagnostic view to the second diagnostic view, the transition comprising a plurality of intermediary three-dimensional representations of the portion, each of the intermediary three-dimensional representations of the portion corresponding to different intermediary viewing angles; and
   displaying a second three-dimensional representation of the second diagnostic view of the portion after the transition, the second three-dimensional representation being at a second viewing angle different than the first viewing angle, the different intermediary viewing angles different than the first and second viewing angles;
   wherein displaying the first three-dimensional representation of the first diagnostic view comprises displaying with a first clipping plane for a first standard two-dimensional representation, wherein displaying the second three-dimensional representation of the second diagnostic view comprises displaying with a second clipping plane for a second standard two-dimensional representation, and wherein animating comprises removing the first clipping plane and adding the second clipping plane to a volume used for rendering the first and second three-dimensional representations.

2. The method of claim 1 wherein receiving an indication comprises receiving user input selecting the second diagnostic view.

3. The method of claim 1 wherein displaying the first three-dimensional representation comprises displaying the first three-dimensional representation statically for at least two seconds, and wherein displaying the second three-dimensional representation comprises displaying the second three-dimensional representation statically for at least two seconds.

4. The method of claim 1 wherein animating comprises generating the plurality of intermediary three-dimensional representations as a sequence, the sequence representing steps in the different viewing angles gradually changing from the first viewing angle to the second viewing angle, each of the intermediary three-dimensional representations being displayed for a short time such that the portion appears to rotate from the first three-dimensional representation to the second three-dimensional representation.

5. The method of claim 1 wherein animating comprises displaying the portion rotating between the first and second diagnostic views.

6. The method of claim 1 wherein the portion comprises a heart, and wherein the transition is from a first multi-planar reconstruction view to a second multi-planar reconstruction view.

7. The method of claim 6 further comprising:
displaying at least three multi-planar reconstruction views including the first and the second at a same time and displaying the first three-dimensional representation, second three-dimensional representation, and intermediary three-dimensional representations with the at least three multi-planar reconstructions.

8. The method of claim 1 wherein the transition occurs in response to a single user input of the indication.

9. The method of claim 1 wherein the transition is from the first diagnostic view to at least a pair of views including the second diagnostic view, the second diagnostic view representing a first sub-portion of the portion represented by the first diagnostic view.

10. The method of claim 9 wherein the transition comprises dividing the first three-dimensional representation into the first sub-portion and a second sub-portion, and separately altering viewing angles for rendering for the first and second sub-portions.

11. The method of claim 1 wherein animating comprises animating transition from the first clipping plane to the second clipping plane.

12. A system for conveying spatial relationships in three-dimensional medical imaging, the system comprising:
a memory operable to store data representing a volume of a patient;
a processor operable to generate a plurality of three-dimensional representations of the volume from the data, each of the three-dimensional representations having a different viewing angle relative to the volume;
a timer operable to cause static display of an initial three-dimensional representation of the plurality for a first period and a final three-dimensional representation of the plurality for a second period, and operable to cause display of a sequence of three-dimensional representations of the plurality between the initial and final three-dimensional representations, each of the three-dimensional representations of the sequence being displayed for a time less than the first and second periods; and
a display operable to display the initial three-dimensional representation, the sequence of three-dimensional representations, and the final three-dimensional representation.
wherein the processor is configured to display the initial three-dimensional representation with a first clipping plane for a first standard two-dimensional representation, to display the final three-dimensional representation with a second clipping plane for a second standard two-dimensional representation, and to display the sequence as removing the first clipping plane and adding the second clipping plane to a volume used for rendering the initial and final three-dimensional representations.

13. The system of claim 12 further comprising:
a user input, the processor operable to transition in an animation from the initial three-dimensional representation, through the sequence of three-dimensional representations, and to the final three-dimensional representation in response to user activation of the user input.

14. The system of claim 12 wherein the processor is operable to generate a multi-planar reconstruction of the volume, the initial and final three-dimensional representations comprising three-dimensional renderings from viewing angles associated with first and second planes of the multi-planar reconstruction, the sequence comprising rotation between the viewing angles.

\* \* \* \* \*